United States Patent [19]

Holtkamp

[11] Plant 4,349

[45] Dec. 19, 1978

[54] AFRICAN VIOLET PLANT

[75] Inventor: Reinhold Holtkamp, Isselburg, Fed. Rep. of Germany

[73] Assignee: Gesellschaftsvertrag uber die Erfindergemeinschaft "Optimara", Isselburg, Fed. Rep. of Germany

[21] Appl. No.: 880,053

[22] Filed: Feb. 22, 1978

[51] Int. Cl.[2] ..... A01H 5/00

[52] U.S. Cl. ..... Plt./69

[58] Field of Search ..... PLT./69

*Primary Examiner*—Robert E. Bagwill

*Attorney, Agent, or Firm*—Beall & Jeffery

[57] ABSTRACT

An African violet known by the varietal name Kansas and a mutation of Delaware, characterized by strong upright flower stems each of which carries 4–5 flowers. The flowers are large, star-shaped, non-dropping and pure white in color, with a slight red hue in center. Kansas flowers continuously, is fast growing, and have a compact growth habit.

1 Drawing Figure

The present invention comprises a new and distinct cultivar of African violet plant, botanically known as *Saintpaulia ionantha,* and hereinafter referred to by the cultivar name Kansas.

Kansas, referred to during the selection process by the numbers 72/76 - 92/77, is a mutation of Delaware, disclosed in my pending application Ser. No. 743,149, filed Nov. 18, 1976. Kansas has the same characteristics as its parent Delaware of large, star-shaped, non-dropping flowers; continuous production strong upright stems, and compact and fast growing habit.

Kansas was discovered and selected by me as a flowering plant in a controlled environment in Isselburg, Rhineland, Germany, as a mutation of the parent cultivar Delaware. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Kansas, which in combination distinguish this African violet as a new and distinct cultivar:

1. Strong, upright flower stems, 60 mm. long.

2. When blooming for the first time, there are 6–8 flower stems with 4–5 large flowers on each stem, thereby providing a full, rich bouquet. Productivity of new stems and flowers is continuous, with the number of stems frequently increasing in subsequent flowerings.

3. The flowers are carried on straight penduncles, which are 20 mm. long.

4. The flowers are very large and star-shaped with five petals of equal size, and are non-dropping. A few flowers have up to seven petals.

5. The flower color is essentially pure white, with red-violet centers. Occasionally, the red-violet color will extend radially from the center, thereby giving the flower a variegated appearance.

The accompanying photographic drawing shows a typical specimen plant of the new cultivar. The colors appearing in the photograph are as true as possible with color illustrations of this type.

In the following description, color references are made to the Royal Horticultural Society color chart (RHS), 1966 edition, except where general color terms of ordinary significance are obvious.

Botanical classification: *Saintpaulia ionantha,* Ramat. cv. Kansas.

Parentage: Mutation of Delaware.

Propagation: The new cultivar holds its distinguishing characteristics through successive propagations by leaf cuttings and by division of shoots.

Plant: From 8 cm. to 9 cm. tall when grown in pots, and approximately 22 cm. in diameter when fully grown.

*Leaves.*—General Form: Oblong — heart shaped. Diameter: 50–60 mm. Texture: soft, velvety. Aspect: Slightly hairy. Veins: Well pronounced. Color (upperside): 137 A. Color (underside): 142 D. Petiole: greenish-white, 142 D.

*Flowers.*—Buds: round shape, diameter 7–8 mm., color 145 C. Sepals: Five in number, 5-6 mm. long, spearshaped. Color: 143 C. Calyx: Flat, funnel shape. Aspect: Receptacle and seed-vessel are fused. Penduncle: Slightly hairy, 20 mm. long, straight.

*Individual flowers.*—Size. 45 -55 mm. in diameter, with the petals being 22–24 mm. long and 17–19 mm. wide. Color: Upperside: 155 D; center, red 66D. Underside: 155 D, with red shining through in center. Borne: The stems carry 4–5 single flowers. Shape: Five petals of equal size and of star shape: occasionally flowers have up to seven petals. Arrangement: On sturdy, upright flower stems, 60 mm. long. Flowering time: 8–9 weeks after potting of small plants, the first buds and flowers show; 9–10 weeks after potting, the plant is in full bloom.

*Reproductive organs.*—Stamens: normally five in number, but occasionally up to seven, almost totally covering the seed vessel. Anthers: 10 anthers, first together, later spreading, color 7 A. Arrangement: The stamens are connected around the seed-vessel with the receptacle by short stems. Filaments: 3–5 mm. long. Styles: 6–8 mm. long. Pollen color: 7 C.

*Roots.*—Delicate, well developed, slightly hairy; roots are white, old roots are brownish.

*Disease resistance.*—No disease problems experienced to date.

*General observations.*—Kansas is fast growing and richly blooming. The very large flowers are star-shaped, and the color pure white, with a red-violet hue in the center, which is irregular. Some flowers have up to seven stamens which almost totally cover the seed vessel. The style emerges in the center out of the seed-vessel and through the stamens. The flower stems carry up to five large single flowers on short peduncles, and the flowers do not drop. Flowering is continuous.

I claim:

1. A new and distinct cultivar of African violet known by the varietal name Kansas and characterized by the combined features of strong upright flower stems each of which carries 4–5 flowers; large, star-shaped, non-dropping flowers pure white in color, with red hue in center; continuous flowering, and fast growing and compact growth habit.

* * * * *

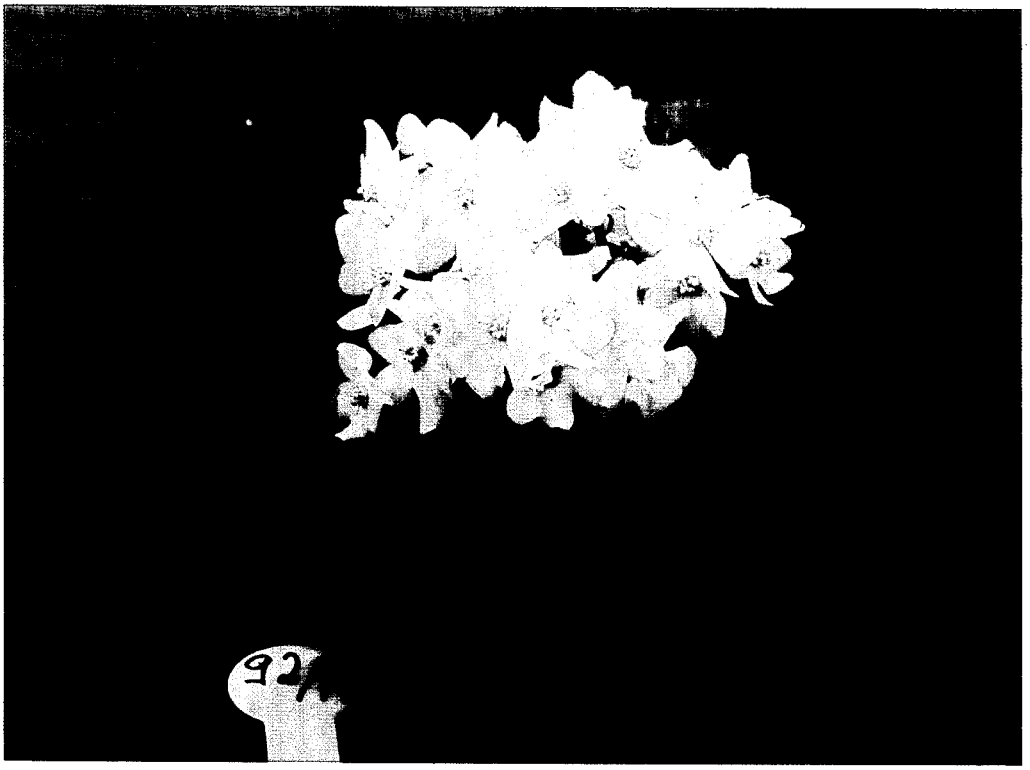
92